(12) United States Patent
Satou et al.

(10) Patent No.: US 10,597,627 B2
(45) Date of Patent: Mar. 24, 2020

(54) APPARATUS FOR PRODUCING ORGANIC SUBSTANCE FROM WASTE AND METHOD FOR PRODUCING ORGANIC SUBSTANCE FROM WASTE

(71) Applicant: SEKISUI CHEMICAL CO., LTD., Osaka (JP)

(72) Inventors: Kanetomo Satou, Tsukuba (JP); Norihide Nishiyama, Tsukuba (JP); Kokoro Hamachi, Tsukuba (JP); Tetsuya Ishii, Tsukuba (JP)

(73) Assignee: SEKISUI CHEMICAL CO., LTD., Osaka (JP)

( * ) Notice: Subject to any disclaimer, the term of this patent is extended or adjusted under 35 U.S.C. 154(b) by 0 days.

(21) Appl. No.: 15/324,408

(22) PCT Filed: Jul. 27, 2015

(86) PCT No.: PCT/JP2015/071225
§ 371 (c)(1),
(2) Date: Jan. 6, 2017

(87) PCT Pub. No.: WO2016/017573
PCT Pub. Date: Feb. 4, 2016

(65) Prior Publication Data
US 2017/0183618 A1 Jun. 29, 2017

(30) Foreign Application Priority Data
Jul. 30, 2014 (JP) .................................. 2014-154673

(51) Int. Cl.
*C12M 1/00* (2006.01)
*C12P 7/08* (2006.01)
*C12P 7/06* (2006.01)

(52) U.S. Cl.
CPC .............. *C12M 43/04* (2013.01); *C12M 1/00* (2013.01); *C12M 21/12* (2013.01); *C12P 7/08* (2013.01); *C12M 29/04* (2013.01); *C12M 29/06* (2013.01); *C12P 7/065* (2013.01)

(58) Field of Classification Search
None
See application file for complete search history.

(56) References Cited

U.S. PATENT DOCUMENTS

| | | | | |
|---|---|---|---|---|
| 5,821,111 A * | 10/1998 | Grady | ........................ | C12P 1/04 435/252.5 |
| 2002/0159929 A1* | 10/2002 | Kaneko | .................. | C07C 29/152 422/140 |
| 2009/0203100 A1* | 8/2009 | Simpson | .................... | C12P 7/14 435/161 |
| 2011/0107663 A1* | 5/2011 | Tirmizi | .................. | C10G 45/02 44/451 |
| 2011/0125118 A1* | 5/2011 | Lynch | ........................ | C12N 1/20 604/367 |
| 2011/0212433 A1* | 9/2011 | Barker | ..................... | C12P 7/065 435/3 |
| 2013/0089899 A1* | 4/2013 | Kurek | ........................ | C12P 7/40 435/134 |
| 2014/0134686 A1* | 5/2014 | Schultz | ...................... | C12P 7/54 435/140 |

FOREIGN PATENT DOCUMENTS

| | | | |
|---|---|---|---|
| JP | 06-098758 | 4/1994 | |
| JP | 2007-82437 | 4/2007 | |
| JP | 2007-82438 | 4/2007 | |
| JP | 2011-500100 | 1/2011 | |
| JP | 2011-512870 | 4/2011 | |
| JP | 2012-516152 | 7/2012 | |
| JP | 2013-544106 | 12/2013 | |
| WO | 2009/058028 | 5/2009 | |
| WO | WO-2009058028 A1 * | 5/2009 | ............ C12M 21/12 |
| WO | 2010/093262 | 8/2010 | |
| WO | 2012/074543 | 6/2012 | |
| WO | 2013/081779 | 6/2013 | |

OTHER PUBLICATIONS

Tiquia-Arashiro, Thermophilic Carboxydotrophs and their Applications in Biotechnology, Springer (2014) (Year: 2014).*
Copeland et al., High Efficiency Syngas Generation (2005) (Year: 2005).*
International Search Report dated Oct. 13, 2015 in International (PCT) Application No. PCT/JP2015/071225. Office Action dated Feb. 25, 2019 in corresponding Chinese patent application No. 201580037815.X, with English translation.
He Guoqing, Food Fermentation & Brewing Technology, pp. 95 to 96, Dec. 2001, with partial translation.
Partial Supplementary European Search Report dated Feb. 12, 2018 in European Application No. 15828110.5.
Phillips et al., "Biological Production of Ethanol from Coal Synthesis Gas; Medium Development Studies", Applied Biochemistry and Biotechnology; Part A: Enzyme Engineering and Biotechnology, vol. 39/40 (1): 559-571 (Sep. 1, 1993).
Office Action dated Dec. 24, 2019 in corresponding Japanese Patent Application No. 2016-538336 with English translation.

* cited by examiner

*Primary Examiner* — Thomas J. Visone
(74) *Attorney, Agent, or Firm* — Wenderoth, Lind & Ponack, L.L.P.

(57) ABSTRACT

The present invention provides an apparatus and a method which can be used for producing an organic substance effectively from a synthesis gas obtained from a waste incinerator. The apparatus 1 for producing an organic substance from waste, comprises a synthesis gas generation furnace 11, a fermenter 13, and a nutrient feeder. The synthesis gas generation furnace 11 generates a synthesis gas by partial oxidation of waste. The fermenter 13 contains a microorganism which produces an organic substance from the synthesis gas. The nutrient feeder 12 feeds a solid or liquid nutrient to the fermenter 13 when an amount of the synthesis gas supplied to the fermenter 13 is insufficient.

6 Claims, 1 Drawing Sheet

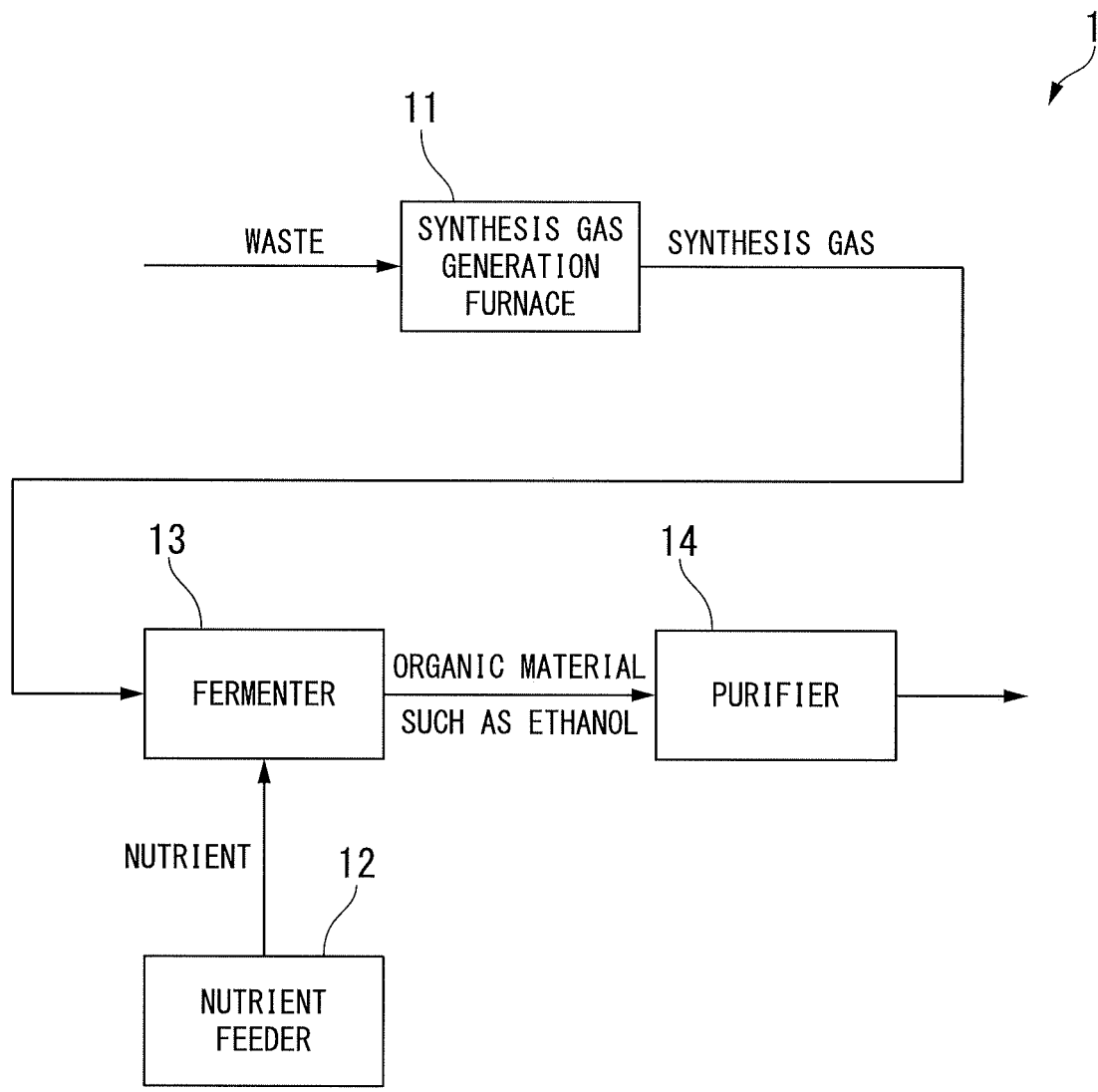

APPARATUS FOR PRODUCING ORGANIC SUBSTANCE FROM WASTE AND METHOD FOR PRODUCING ORGANIC SUBSTANCE FROM WASTE

TECHNICAL FIELD

The present invention relates to an apparatus for producing an organic substance from waste and a method for producing an organic substance from waste.

DESCRIPTION OF RELATED ART

In recent years, researches have been made for practical implementation of a method for producing a chemical substance such as ethanol by microbial fermentation of a carbon monoxide-containing synthesis gas acquired from an exhaust gas from a steelworks and the like (see, for example, Patent Document 1).

DOCUMENTS OF RELATED ART

[Patent Document]
[Patent Document 1] Japanese Unexamined Patent Application Publication (Translation of PCT Application) No. 2011-500100

SUMMARY OF THE INVENTION

Problems to be Solved by the Invention

However, heretofore, a practically applicable apparatus for producing an organic substance from waste has not yet been developed, and the fact is that even sufficient research thereon has not been made.

Various wastes are put into a waste incinerator. Therefore, it is necessary to perform maintenance frequently. The maintenance usually takes several days. Accordingly, the synthesis of an organic substance from a synthesis gas obtained from the waste incinerator may encounter a peculiar problem that the supply of the synthesis gas is suspended for a long period extending to several days.

Therefore, in the case of synthesizing an organic substance using a synthesis gas obtained from a waste incinerator, the possible long-term suspension of the supply of the synthesis gas must be taken into consideration.

For example, Patent Document 1 describes that a storage tank for storing synthesis gas is provided. However, even though a storage tank is provided, the synthesis gas stored in the storage tank alone is not enough to continuously supply the synthesis gas to a fermenter in the case of a long-term suspension of the supply of the synthesis gas from the waste incinerator to the fermenter which may extend, for example, to a period of one day or more. This may results in adverse effects such as death of microorganisms in the fermenter.

For example, it is conceivable to preserve microorganisms at a low temperature. However, it is difficult to preserve microorganisms at a low temperature over a long period of, for example, one day or more.

It is a primary object of the present invention to provide an apparatus and a method which can be used for producing an organic substance effectively from a synthesis gas obtained from a waste incinerator.

Means to Solve the Problems

With respect to the apparatus of the present invention for producing an organic substance from waste, the apparatus comprises a synthesis gas generation furnace, a fermenter and a nutrient feeder. The synthesis gas generation furnace generates a synthesis gas by partial oxidation of the waste. The fermenter contains a microorganism which produces an organic substance from the synthesis gas. The nutrient feeder feeds a solid or liquid nutrient to the fermenter when an amount of the synthesis gas supplied to the fermenter is insufficient.

In the apparatus of the present invention, it is preferred that the nutrient feeder feeds the nutrient to the fermenter when the amount of the synthesis gas supplied to the fermenter is insufficient for one day or more.

In the apparatus of the present invention, it is preferred that the nutrient contains at least one of sugars, carbon dioxide and formic acid.

In the apparatus of the present invention, it is preferred that the microorganism is an anaerobic carboxydotrophic bacterium.

DETAILED DESCRIPTION OF THE INVENTION

With respect to the method of the present invention for producing an organic substance from waste, the method comprises: a synthesis gas generation step of generating a synthesis gas by partial oxidation of waste in a synthesis gas generation furnace; a step of allowing a microorganism to produce an organic substance from the synthesis gas in a fermenter; and a nutrient feeding step of feeding the solid or liquid nutrient to the fermenter when an amount of the synthesis gas supplied to the fermenter is insufficient.

In the method of the present invention, it is preferred that the solid or liquid nutrient is fed to the fermenter in the nutrient feeding step when the amount of the synthesis gas supplied to the fermenter is insufficient for one day or more.

In the method of the present invention, it is preferred that the nutrient contains at least one of sugars, carbon dioxide, and formic acid.

In the method of the present invention, it is preferred that the microorganism is an anaerobic carboxydotrophic bacterium.

Effect of the Invention

As described above, the present invention can provide an apparatus and a method which can be used for effectively producing an organic substance from a synthesis gas obtained from a waste incinerator.

BRIEF DESCRIPTION OF THE DRAWINGS

FIG. 1 is a schematic view of the apparatus for producing an organic substance from waste according to one embodiment of the present invention.

DESCRIPTION OF THE EMBODIMENTS

Hereinbelow, the present invention will be described in detail with reference to preferred embodiments of the present invention. However, these embodiments are only examples. The present invention is in no way limited by these embodiments.

FIG. 1 is a schematic view of the apparatus for producing an organic substance from waste. The apparatus 1 shown in FIG. 1 is an apparatus for producing an organic substance from waste including waste plastic and the like. For example, the organic substance to be produced may be alcohols, organic acids, fatty acids, fats and oils, ketones, biomass, saccharides and the like. More specific examples of the organic substance include ethanol, acetic acid, butanediol and the like.

The obtained organic substance may be used for any purposes without any limitation. For example, the obtained organic substance can be used not only as a material for plastic, resin and the like, but also as fuel.

The apparatus 1 comprises a synthesis gas generation furnace 11, a fermenter 13, a purifier 14 and a nutrient feeder 12. A waste containing organic substances such as plastic and resin is fed into the synthesis gas generation furnace 11. In the synthesis gas generation furnace 11, the waste is partially oxidized so as to generate a synthesis gas. Generally, the obtained synthesis gas contains hydrogen gas and nitrogen gas in addition to carbon monoxide.

The synthesis gas generation furnace 11 is connected to the fermenter 13. The synthesis gas obtained from the synthesis gas generation furnace 11 is fed into the fermenter 13. The fermenter 13 contains a microorganism. The microorganism produces a target organic substance from the synthesis gas. As specific examples of the microorganism preferably used for producing an alcohol such as ethanol, anaerobic carboxydo-trophic bacteria such as *Clostridium* genus and the like can be mentioned.

The fermenter 13 is connected to the purifier 14. Then, the products in the fermenter 13 are transferred to the purifier 14. Generally, the products in the fermenter 13 include another organic substance in addition to the target organic substance. The purifier 14 purifies the products transferred from the fermenter 13. In such a manner as described above, the target organic substance can be obtained.

Incidentally, various wastes are put into the waste incinerator. Therefore, it is necessary to perform maintenance frequently. The maintenance usually takes several days. This causes the supply of the synthesis gas to the fermenter 13 to be suspended for several days, which may have harmful influences on the microorganism contained in the fermenter 13 such as death or denaturation of the microorganism.

As a countermeasure for such a problem, the apparatus 1 of the present invention comprises the nutrient feeder 12. The nutrient feeder 12 feeds the nutrient to the fermenter 13 when an amount of the synthesis gas supplied to the fermenter 13 is insufficient. Therefore, even when the supply of the synthesis gas is suspended, adverse effects on the microorganism can be reduced. Consequently, the apparatus 1 of the present invention can effectively produce an organic substance from a synthesis gas obtained from a waste incinerator.

Further, the nutrient feeder 12 supplies a solid or liquid nutrient to the fermenter 13. Therefore, it is possible to reduce the storage space for the nutrient as compared to the case of supplying a nutrient in a gas state. In other words, a larger amount of nutrients can be stored in a smaller space. Therefore, even when the supply of the synthesis gas is suspended for a long period, for example, extending to one day or more, the adverse effects on the microorganism can be reduced.

For example, keeping the fermenter 13 at a low temperature may be an option for reducing the adverse effects on the microorganism. However, with such an approach, it is difficult to reduce the adverse effects on the microorganism over a long period of time. On the other hand, as described in the present embodiment, feeding the nutrient to the fermenter 13 from the nutrient feeder 12 can reduce the adverse effects on microorganisms over a long period of time.

It is preferred that the solid or liquid nutrient contains at least one of saccharides, carbon dioxide and formic acid. Particularly, it is more preferred that the nutrient contains a saccharide(s). Examples of saccharides suitably used in the present embodiment include hexose and pentose. Examples of the hexose include fructose, glucose, mannose, rhamnose and the like. Examples of pentoses include arabinose, ribose, xylose and the like.

The present embodiment has been explained above, taking as an example the apparatus 1 comprising the synthesis gas generation furnace 11. However, the present invention is in no way limited to such a configuration. The synthesis gas generation furnace may be provided separately from the apparatus 1 shown in FIG. 1.

DESCRIPTION OF THE REFERENCE SIGNS

1: Apparatus 1
11: Synthesis gas generation furnace
12: Nutrient feeder
13: Fermenter
14: Purifier

What is claimed is:

1. A method for producing an alcohol, comprising:
a synthesis gas generation step of generating a synthesis gas by partial oxidation of waste in a synthesis gas generation furnace, which is to be subjected to a maintenance periodically;
a step of allowing a microorganism to produce an alcohol from the synthesis gas in a fermenter, the microorganism being an anaerobic carboxydotrophic bacterium belonging to the genus *Clostridium*, with the proviso that supply of the synthesis gas to the fermenter is suspended during the maintenance of the synthesis gas generation furnace; and
a nutrient feeding step of feeding a solid or liquid nutrient to the fermenter with a nutrient feeder configured to feed the solid or liquid nutrient to the fermenter only when an amount of the synthesis gas supplied to the fermenter is insufficient during the maintenance of the synthesis gas generation furnace.

2. The method according to claim 1, wherein the solid or liquid nutrient is fed to the fermenter in the nutrient feeding step only when the amount of the synthesis gas supplied to the fermenter is insufficient for one day or more.

3. The method according to claim 1, wherein the nutrient containing at least one of sugars, carbon dioxide and formic acid.

4. The method according to claim 1, wherein the alcohol is ethanol.

5. The method according to claim 1, wherein the nutrient feeder is configured to feed all of the solid or liquid nutrient to be fed to the fermenter.

6. The method according to claim 2, wherein the nutrient containing at least one of sugars, carbon dioxide and formic acid.

* * * * *